United States Patent
Liu et al.

(10) Patent No.: US 8,080,522 B2
(45) Date of Patent: Dec. 20, 2011

(54) POLYETHLENE GLYCOL MODIFICATIONS OF THYMOSIN ALPHA-1

(75) Inventors: Keliang Liu, Beijing (CN); Jiankun Qie, Beijing (CN); Jinbo Ma, Beijing (CN); Jianquan Zheng, Beijing (CN); Sijian Dong, Beijing (CN); Wenxia Zhou, Beijing (CN); Chunhui Qi, Beijing (CN)

(73) Assignee: Institute of Pharmacology and Toxicology Academy of Military Mecical Sciences, P.L.A., China, Beijing (CN)

( * ) Notice: Subject to any disclaimer, the term of this patent is extended or adjusted under 35 U.S.C. 154(b) by 453 days.

(21) Appl. No.: 12/093,240

(22) PCT Filed: Nov. 11, 2006

(86) PCT No.: PCT/CN2006/003021
§ 371 (c)(1),
(2), (4) Date: Sep. 22, 2008

(87) PCT Pub. No.: WO2007/054030
PCT Pub. Date: May 18, 2007

(65) Prior Publication Data
US 2009/0221487 A1      Sep. 3, 2009

(30) Foreign Application Priority Data
Nov. 10, 2005   (CN) .......................... 2005 1 0117752

(51) Int. Cl.
*C07K 14/575* (2006.01)
*A61K 38/22* (2006.01)

(52) U.S. Cl. ....... 514/12.9; 514/21.3; 530/324; 530/399

(58) Field of Classification Search .................. None
See application file for complete search history.

(56) References Cited

FOREIGN PATENT DOCUMENTS

| CN | 1532207 | 9/2004 |
| CN | 1690079 | 11/2005 |
| WO | WO 03037272 | 5/2003 |

OTHER PUBLICATIONS

Huijuan et al. CN1690079. English translation of the Chinese Patent. Nov. 2005.*
Keliang et al. CN1532207. English Translation of Chinese Patent. Sep. 2004.*
Ou-Yang et al. "Co-Delivery of GM-CSF Gene Enhances the Immune Responses of Hepatitis C Viral Core Protein-Expressing DNA Vaccine: Role of Dendritic Cells." J. of Med. Virol. vol. 66, pp. 320-328. 2002.*
Encke et al. :"Development of a heterologous, multigenotype vaccine against hepatitis C virus infection" Europ. J. of Clin. Inves. vol. 37, pp. 396-406. 2007.*
Abrignani et al. Perspectives for a vaccine against hepatitis C virus. J. of Hepatology. vol. 31, Supp. 1, pp. 259-263. 1999.*
Houghton et al. Prospects for a Vaccine against the Hepatitis C virus. Nature, vol. 436, pp. 961-966. Aug. 2005.*
Bain et al. Effects of HCV Viral Dynamics on Treatment Design: Lessons Learned from HIV. American Journal of Gastroenterology. vol. 96, No. 10, pp. 2818-2828. 2001.*
Hunt, Richard. "Virology—Chapter Twenty Five, Corona Viruses, Colds and SARS." Retrieved from the Internet <URL:http://pathmicro.med.sc.edu/virol/coronaviruses.htm>. Apr. 6, 2010. Retrieved Feb. 14, 2011.*
Braun et al. "Setting the stage for bench-to-bedside movment of anti-HIV RNA inhibitors-gene therapy for AIDS in macaques" Frontiers in Bioscience, vol. 11, pp. 838-851, Jan. 2006.*
Gait et al. "Progress in anti-HIV structure based drug design." TIBTECH, vol. 13. pp. 430-438, Oct. 1995.*
Holmes, Kathryn. "SARS coronavirus: a new challenge for prevention and therapy." J. Clin. Invest. 111:1605-1609 (2003).*

* cited by examiner

*Primary Examiner* — Anish Gupta
(74) *Attorney, Agent, or Firm* — Alston & Bird LLP

(57) ABSTRACT

Polyethylene glycol modifications of thymosin alpha 1 (Tα 1-PEGs), their preparation process, the medicine composition containing them, and their application in the medicine for preventing and treating diseases related with immune deficiency and hypoimmunity, including hepatitis B, hepatitis C, hepatoma, malignant melanoma, non-small cell lung cancer, SARS, and AIDS etc.

14 Claims, 3 Drawing Sheets

POLYETHLENE GLYCOL MODIFICATIONS OF THYMOSIN ALPHA-1

CROSS-REFERENCE TO RELATED APPLICATIONS

This application is the U.S. National Stage of International Application PCT/CN2006/003021, filed Nov. 10, 2006, which claims the benefit under 35 U.S.C. §119(a) of CN 200510117752.7, filed Nov. 10, 2005; both of which are hereby incorporated herein in their entirety by reference.

TECHNICAL FIELD

The invention relates to polyethylene glycol modifications of Thymosin alpha 1 (Tα1-PEGs), the process for preparing Tα1-PEGs, a pharmaceutical composition containing them, and use of them for the manufacture of a medicament, which is administrated alone or in combination with other medicaments, for the prevention and treatment of diseases related to immune deficiency or hypoimmunity including hepatitis B, hepatitis C, hepatoma, malignant melanoma, non-small cell lung cancer, SARS (severe acute respiratory syndrome) caused by coronavirus, and HIV etc.

BACKGROUND ART

Thymosin alpha 1 (Tα1) is one of the active peptides secreted by thymus gland, and has highly conserved sequence and the Tα1 from different species has the same chemical structure. Tα1 is consisted of 28 amino acid residues, having a molecular weight of 3108 and an isoelectric point of 4.2, and it's N-terminal is acetylated. The primary structure of Tα1 is:

```
            1                                  10
Ac-Ser-Asp-Ala-Ala-Val-Asp-Thr-Ser-Ser-Glu-Ile-

20
Thr-Thr-Lys-Asp-Leu-Lys-Glu-Lys-Lys-Glu-Val-Val-

28
Glu-Glu-Ala-Glu-Asn-OH
```

Tα1 is known as an immunopotentiator to T lymphocytes and it can promote T cell maturation and differentiation, induce mature T cell secreting several lymphokines (such as interleukin-2 and interferon-γ), and induce the generation of interleukin-2 receptor. In addition, Tα1 has direct inhibiting or killing effect on the growth of some virus infected cells and tumor cells. As for immunopotentiator, Tα1 is effective in treating diseases related to immune deficiency or hypoimmunity. Clinical trail for Tα1 started at 1980's. Tα1 is also effective and safe in treating chronic hepatitis B when is used alone or in combination with interferon. For several other diseases such as hepatitis C, hepatoma, malignant melanoma, non-small cell lung cancer, and HIV etc., Tα1 is also effective. Moreover, Tα1 can be used as vaccine supplement to increase the effect of influenza and hepatitis B vaccine.

Tα1 currently used in clinical is a synthetic chemical as a formulation of sterilized dry powder. The dosage for the treatment of chronic hepatitis B is 1.6 mg per dose for twice one week by injecting 2, and the course of treatment is 6 months. This treatment has shortcomings such as high-dose, frequently injections and high cost. So it is important to improve the metabolism of Tα1 in vivo, to increase the bioavailability, to prolong the effectiveness and to find long-acting Tα1 analogues.

CONTENTS OF THE INVENTION

The inventors had found that modified product of Tα1, covalently modified with polyethylene glycol (PEG), has significant improvement in bioavailability in vivo and has prolonged effectiveness in vivo, and keeps potent immuno enhancement activity as well.

The invention relates to PEG modifications of Tα1 of Formula (I):

$$Z\text{-}[Cys^x(PEG\text{-}M)]\text{-}(Aa)_n\text{-}T \qquad (I)$$

wherein,

M = (MAL structure shown), or $-\overset{O}{\underset{O}{\overset{\|}{S}}}-CH_2-CH_2-$, or $-NH-\overset{O}{\underset{}{\overset{\|}{C}}}-$ ;

Z=H, methyl, ethyl, propyl, isopropyl, butyl, pentyl, isopentyl, formyl, acetyl, propionyl, carbamoyl, benzyloxycarbonyl, fluorenylformyl etc., preferably acetyl, carbamoyl;

PEG is $RO(CH_2CH_2O)_m-CH_2CH_2-$, R=H or $CH_3$, m=5-2000;

Cys is cysteine and covalently linked with M group via side chain sulfide atom; when n=0, carboxyl of Cys is linked with N-terminal amino group of T by an amide linkage, or amino group of Cys is linked with C-terminal carboxyl of T by an amide linkage; Cys can be at both terminals of T sequence, or in between any adjacent amino acids, or replace amino acids at any sites; when n=1-10, Cys can be linked with N-terminal or C-terminal of T sequence via Aa;

Aa is any one of 20 natural amino acids or any combinations thereof, wherein said natural amino acids include Ala, Arg, Asn, Asp, Cys, Gln, Glu, Gly, His, Ile, Leu, Lys, Met, Phe, Pro, Ser, Thr, Trp, Tyr, Val etc., preferably Aa is Gly, Ala, Val, Leu;

T represents a natural Tα1 complete sequence or an analogue thereof in which any site is substituted by at least one Cys.

In a further aspect, the invention relates to a pharmaceutical composition comprising at least one compound of formula (I) and pharmaceutically acceptable carriers or excipients.

In a further aspect, the invention relates to use of at least one of the compounds of formula (I) for the manufacture of a medicament for the prevention and treatment of diseases related to immune deficiency or hypoimmunity including hepatitis B, hepatitis C, hepatoma, malignant melanoma, non-small cell lung cancer, SARS caused by coronavirus, and HIV etc.

The configurations of amino acids in the invention are L-amino acids except indicating D-amino acids. According to the invention, PEG modifiers are commercially available reagents and the average molecular weights of the PEG modifiers are from several hundreds to several ten thousands.

Tα1 complete sequence can be synthesized by conventional solid-phase or liquid-phase polypeptide synthesis. During the synthesis, it is very easy to add Cys to N-terminal or C-terminal or any site in Tα1 sequence or replace any amino acid in Tα1 sequence with Cys. After synthesis, dissolve peptide chain containing Cys in water, adjust pH to near neutral, and add PEG modifiers, and purify by HPLC to give rise to Tα1-PEGs.

The invention use solid-phase polypeptide synthesis to add Cys to any site in Tα1 sequence, giving rise to T derivatives of formula Z-[Cys$^x$]-(Aa)$_n$-T, which are cleaved and purified and then reacted with PEG modifiers with average molecular weight of 750, 1100, 2000 and 5000. Purify the product by HPLC, and lyophilize the product, giving rise to Z-[Cys$^x$(PEG-M)]-(Aa)n-T. HPLC analysis of the product shows only one peak, and biological mass spectrometry analysis of the product shows correct structures.

According to the invention, the pharmaceutical composition of the invention can be made to any formulations suitable for any mammals, such as injection with mannitol as excipient.

According to the invention, the term "analogue" means a Tα1 sequence formed from the natural Tα1 complete sequence which is substituted at any site with at least one Cys.

According to the invention, PEG$_{5000}$ in the specification means PEG whose average molecular weight is 5000.

According to the invention, the preferable Tα1 sequences and Cys derivatives thereof are shown below:

BMJBT001:
Ac-Ser-Asp-Ala-Ala-Cys-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT002:
Ac-Ser-Asp-Ala-Ala-Val-Asp-Thr-Cys-Ser-Glu-Ile-Thr-Thr-Lys-Asp-Leu-Lys-Glu-Lys-Lys-Glu-Val-Val-Glu-Glu-Ala-Glu-Asn-OH

BMJBT003:
Ac-Ser-Asp-Ala-Ala-Val-Asp-Thr-Ser-Ser-Glu-Cys-Thr-Thr-Lys-Asp-Leu-Lys-Glu-Lys-Lys-Glu-Val-Val-Glu-Glu-Ala-Glu-Asn-OH

BMJBT004:
Ac-Ser-Asp-Ala-Ala-Val-Asp-Thr-Ser-Ser-Glu-Ile-Thr-Thr-Lys-Asp-Cys-Lys-Glu-Lys-Lys-Glu-Val-Val-Glu-Glu-Ala-Glu-Asn-OH

BMJBT005:
Ac-Ser-Asp-Ala-Ala-Val-Asp-Thr-Ser-Ser-Glu-Ile-Thr-Thr-Lys-Asp-Leu-Cys-Glu-Lys-Lys-Glu-Val-Val-Glu-Glu-Ala-Glu-Asn-OH

BMJBT006:
Ac-Ser-Asp-Ala-Ala-Val-Asp-Thr-Ser-Ser-Glu-Ile-Thr-Thr-Lys-Asp-Leu-Lys-Glu-Lys-Lys-Cys-Val-Val-Glu-Glu-Ala-Glu-Asn-OH

BMJBT007:
Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Cys-Glu-Ala-Glu-Asn-OH

BMJBT008:
Ac-Cys-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT009:
Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-Cys-NH$_2$

BMJBT010:
Ac-Cys-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT011:
Ac-Ser-Cys-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT012:
Ac-Ser-Asp-Cys-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT013:
Ac-Ser-Asp-Ala-Cys-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT014:
Ac-Ser-Asp-Ala-Ala-Val-Cys-Thr-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT015:
Ac-Ser-Asp-Ala-Ala-Val-Asp-Cys-Ser-Ser-Glu-Ile-Thr-Thr-Lys-Asp-Leu-Lys-Glu-Lys-Lys-Glu-Val-Val-Glu-Glu-Ala-Glu-Asn-OH

BMJBT016:
Ac-Ser-Asp-Ala-Ala-Val-Asp-Thr-Ser-Cys-Glu-Ile-Thr-Thr-Lys-Asp-Leu-Lys-Glu-Lys-Lys-Glu-Val-Val-Glu-Glu-Ala-Glu-Asn-OH

BMJBT017:
Ac-Ser-Asp-Ala-Ala-Val-Asp-Thr-Ser-Cys-Ile-Thr-Thr-Lys-Asp-Leu-Lys-Glu-Lys-Lys-Glu-Val-Val-Glu-Glu-Ala-Glu-Asn-OH

BMJBT018:
Ac-Ser-Asp-Ala-Ala-Val-Asp-Thr-Ser-Ser-Glu-Cys-Thr-Thr-Lys-Asp-Leu-Lys-Glu-Lys-Lys-Glu-Val-Val-Glu-Glu-Ala-Glu-Asn-OH

BMJBT019:
Ac-Ser-Asp-Ala-Ala-Val-Asp-Thr-Ser-Ser-Glu-Ile-Thr-Cys-Lys-Asp-Leu-Lys-Glu-Lys-Lys-Glu-Val-Val-Glu-Glu-Ala-Glu-Asn-OH

BMJBT020:
Ac-Ser-Asp-Ala-Ala-Val-Asp-Thr-Ser-Ser-Glu-Ile-Thr-Thr-Cys-Asp-Leu-Lys-Glu-Lys-Lys-Glu-Val-Val-Glu-Glu-Ala-Glu-Asn-OH

BMJBT021:
Ac-Ser-Asp-Ala-Ala-Val-Asp-Thr-Ser-Ser-Glu-Ile-Thr-Thr-Lys-Cys-Leu-Lys-Glu-Lys-Lys-Glu-Val-Val-Glu-Glu-Ala-Glu-Asn-OH

BMJBT022:
Ac-Ser-Asp-Ala-Ala-Val-Asp-Thr-Ser-Ser-Glu-Ile-Thr-Thr-Lys-Asp-Leu-Lys-Cys-Lys-Lys-Glu-Val-Val-Glu-Glu-Ala-Glu-Asn-OH

BMJBT023:
Ac-Ser-Asp-Ala-Ala-Val-Asp-Thr-Ser-Ser-Glu-Ile-Thr-Thr-Lys-Asp-Leu-Lys-Glu-Cys-Lys-Glu-Val-Val-Glu-Glu-Ala-Glu-Asn-OH

BMJBT024:
Ac-Ser-Asp-Ala-Ala-Val-Asp-Thr-Ser-Ser-Glu-Ile-Thr-Thr-Lys-Asp-Leu-Lys-Glu-Lys-Cys-Glu-Val-Val-Glu-Glu-Ala-Glu-Asn-OH

BMJBT025:
Ac-Ser-Asp-Ala-Ala-Val-Asp-Thr-Ser-Ser-Glu-Ile-Thr-Thr-Lys-Asp-Leu-Lys-Glu-Lys-Lys-Glu-Cys-Val-Glu-Glu-Ala-Glu-Asn-OH

BMJBT026:
Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Cys-Glu-Glu-Ala-Glu-Asn-OH

-continued

BMJBT027:
Ac-Ser-Asp-Ala-Ala-Val-Asp-Thr-Ser-Ser-Glu-Ile-
Thr-Thr-Lys-Asp-Leu-Lys-Glu-Lys-Lys-Glu-Val-Val-
Glu-Cys-Ala-Glu-Asn-OH

BMJBT028:
Ac-Ser-Asp-Ala-Ala-Val-Asp-Thr-Ser-Ser-Glu-Ile-
Thr-Thr-Lys-Asp-Leu-Lys-Glu-Lys-Lys-Glu-Val-Val-
Glu-Glu-Cys-Glu-Asn-OH

BMJBT029:
Ac-Ser-Asp-Ala-Ala-Val-Asp-Thr-Ser-Ser-Glu-Ile-
Thr-Thr-Lys-Asp-Leu-Lys-Glu-Lys-Lys-Glu-Val-Val-
Glu-Glu-Ala-Cys-Asn-OH

BMJBT030:
Ac-Ser-Asp-Ala-Ala-Val-Asp-Thr-Ser-Ser-Glu-Ile-
Thr-Thr-Lys-Asp-Leu-Lys-Glu-Lys-Lys-Glu-Val-Val-
Glu-Glu-Ala-Glu-Cys-OH

According to the invention, the preferable PEG modifications of Tα1 are shown below:
BTJB005,
BTJB006,
BTJB007,
BTJB008,
BTJB009,
BTJB010,
BTJB011,
BTJB012,
BTJB013,
BTJB014,
BTJB015,
BTJB016,
BTJB017,
BTJB018,
BTJB019,
BTJB020,
BTJB021,
BTJB022,
BTJB023,
BTJB024.

According to the invention, the symbol "BMJBT" means a Tα1 sequence which is substituted with one Cys at any site, and the symbol "BMJB" means PEG modified BMJBT.

Figure 1:
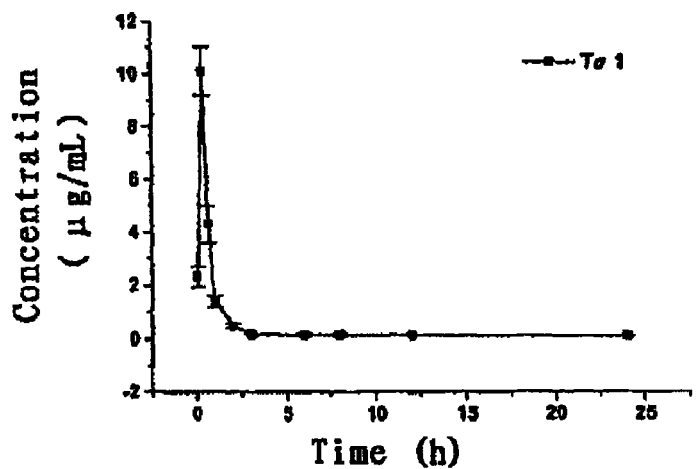
FIG. 1 Plasma concentration—time curve of Tα1 in mouse.

The abbreviations used in the invention have the meanings following:
Tα1—thymosin α1
PEG—polyethylene glycol
Ala—alanine
Arg—arginine
Asn—asparagines
Asp—aspartic acid
Cys—cysteine
Gln—glutamine
Glu—glutamic acid
Gly—glycine
His—histidine
Ile—isoleucine
Leu—leucine
Lys—lysine
Met—methionine
Phe—phenylalanine
Pro—proline
Ser—serine
Thr—threonine
Trp—tryptophan
Tyr—tyrosine
Val—valine
Ac—acetyl
MAL—maleimide
Fmoc—fluorenylmethoxycarbonyl
DMF—dimethylformamide
DCC—dicyclohexylcarbodiimide
HBTU—2-(1H-Benzotriazole-1-yl)-1,1,3,3-tetramethyluronium hexafluorophosphate
HOBt—1-hydroxybenzotriazole
HOSu—N-hydroxysuccinimide
NMM—N-methylmorpholine
TFA—trifluoroacetic acid
TsCl—p-toluene sulfonyl chloride
EDT—ethane-1,2-dithiol
RP-HPLC—reversed phase high performance liquid chromatography
IFN-γ—interferon-γ

MODE OF CARRYING OUT THE INVENTION

Example

The following Examples represent illustrative modes of carrying out the invention, but the invention is not restricted in these Examples. The mPEG modifiers having average molecular weights of 2000 to 85000 and Wang resin for solid-phase synthesis used in the Examples are products of Nankai Systhesis, and TFA, Rink amide resin, DCC, HOBt, Fmoc-amino acids are products of GL Biochem (Shanghai) Ltd.

Example 1

Ac-[Cys$^5$(mPEG$_{5000}$-MAL)]Tα1 (BTJB005)

1.1 The Synthesis of Ac-[Cys$^5$]Tα1

Synthesize [Cys$^5$]Tα1 by using solid-phase polypeptide synthesis: Wang resin 100 mg was used as solid phase carrier, Fmoc-AA-OH (1-10 times of Wang resin load) was used as starting material, and DCC (1-10 times of Wang resin load) and HOBt (1-10 times of Wang resin load) were used as condensing agent. The amino acids were coupled according to the sequence of Tα1 except that the Val$^5$ was replaced by Cys$^5$, giving rise to side chain fully protected Ac-[Cys$^5$]Tα1 resin. After drying the resin, cleavage was performed by TFA at room temperature for 20-200 minutes. Filter off the resin and add ethyl ether to precipitate, giving rise to white solid. Dissolve the whit solid in water, and then lyophilize it, giving rise to 161 mg white solid. Purify the solid by RP-HPLC, and analyze it by ESI-MS. $[M]^{2+}$ peak: 1551.0 (theoretical value: 3098).

1.2 The Synthesis of Ac-[$Cys^5$(mPEG$_{5000}$-MAL)]Tα1

Dissolve the purified Ac-[$Cys^5$]Tα1 in water and adjust pH to 5-10. Add mPEG$_{5000}$ modifiers and react at room temperature. Separate the product by RP-HPLC and lyophilize it, giving rise to 17.8 mg white solid with a yield of 38.2%.

The product Ac-[$Cys^5$(mPEG$_{5000}$-MAL)]Tα1 was analyzed by MALDI-TOF-MS. There are several peaks around 8373, the difference of molecular weight between two adjacent two peaks are about 44, which is the typical structural characteristic of polyethylene glycol.

Example 2

Ac-[$Cys^8$(mPEG$_{5000}$-MAL)]Tα1 (BMJB008)

Use the same method as described in Example 1.1 to synthesize Ac-[$Cys^8$]Tα1, giving rise to crude peptide 116 mg. Purify it by RP-HPLC and analyze it by ESI-MS. $[M]^{2+}$ peak: 1543.0 (theoretical value: 3083).

Use the same method as described in Example 1.2 to synthesize Ac-[$Cys^8$(mPEG$_{5000}$-MAL)]Tα1. Purify the product by HPLC and lyophilize it, giving rise to 16.9 mg white solid with a yield of 37.1%.

Use MALDI-TOF-MS to analyze Ac-[$Cys^8$(mPEG$_{5000}$-MAL)]Tα1. There are several peaks around 8247, the difference of molecular weight between adjacent two peaks are about 44, which is the typical structural characteristic of polyethylene glycol.

Example 3

Ac-[$Cys^{11}$(mPEG$_{5000}$-MAL)]Tα1 (BMJB011)

Use the same method as described in Example 1.1 to synthesize Ac-[$Cys^{11}$]Tα1, giving rise to crude peptide 143 mg. Purify it by RP-HPLC and analyze it by ESI-MS. $[M]^{3+}$ peak: 1034.9 (theoretical value: 3098).

Use the same method as described in Example 1.2 to synthesize Ac-[$Cys^{11}$(mPEG$_{5000}$-MAL)]Tα1. Purify the product by HPLC and lyophilize it, giving rise to 21.4 mg white solid with a yield of 28.9%.

Use MALDI-TOF-MS to analyze Ac-[$Cys^{11}$(mPEG$_{5000}$-MAL)]Tα1. There are several peaks around 8282, the difference of molecular weight between adjacent two peaks are about 44, which is the typical structural characteristic of polyethylene glycol.

Example 4

Ac-[$Cys^{16}$(mPEG$_{5000}$-MAL)]Tα1 (BMJB016)

Use the same method as described in Example 1.1 to synthesize Ac-[$Cys^{16}$]Tα1, giving rise to crude peptide 147 mg. Purify it by RP-HPLC and analyze it by ESI-MS. $[M]^{3+}$ peak: 1034.0 (theoretical value: 3098).

Use the same method as described in Example 1.2 to synthesize Ac-[$Cys^{16}$(mPEG$_{5000}$-MAL)]Tα1. Purify the product by HPLC and lyophilize it, giving rise to 15.6 mg white solid with a yield of 53.3%.

Use MALDI-TOF-MS to analyze Ac-[$Cys^{16}$(mPEG$_{5000}$-MAL)]Tα1. There are several peaks around 8296, the difference of molecular weight between adjacent two peaks are about 44, which is the typical structural characteristic of polyethylene glycol.

Example 5

Ac-[$Cys^{17}$(mPEG$_{5000}$-MAL)]Tα1 (BMJB017)

Use the same method as described in Example 1.1 to synthesize Ac-[$Cys^{17}$]Tα1, giving rise to crude peptide 133 mg. Purify it by RP-HPLC and analyze it by ESI-MS. $[M]^{3+}$ peak: 1029.6 (theoretical value: 3083).

Use the same method as described in Example 1.2 to synthesize Ac-[$Cys^{17}$(mPEG$_{5000}$-MAL)]Tα1. Purify the product by HPLC and lyophilize it, giving rise to 17.4 mg white solid with a yield of 42.6%.

Use MALDI-TOF-MS to analyze Ac-[$Cys^{17}$(mPEG$_{5000}$-MAL)]Tα1. There are several peaks around 8237, the difference of molecular weight between adjacent two peaks are about 44, which is the typical structural characteristic of polyethylene glycol.

Example 6

Ac-[$Cys^{21}$(mPEG$_{5000}$-MAL)]Tα1 (BMJB021)

Use the same method as described in Example 1.1 to synthesize Ac-[$Cys^{21}$]Tα1, giving rise to crude peptide 166 mg. Purify it by RP-HPLC and analyze it by ESI-MS. $[M]^{3+}$ peak: 1029.0 (theoretical value: 3082).

Use the same method as described in Example 1.2 to synthesize Ac-[$Cys^{21}$(mPEG$_{5000}$-MAL)]Tα1. Purify the product by HPLC and lyophilize it, giving rise to 28.3 mg white solid with a yield of 49.3%.

Use MALDI-TOF-MS to analyze Ac-[$Cys^{21}$(mPEG$_{5000}$-MAL)]Tα1. There are several peaks around 8263, the difference of molecular weight between adjacent two peaks are about 44, which is the typical structural characteristic of polyethylene glycol.

Example 7

Ac-[$Cys^{24}$(mPEG$_{5000}$-MAL)]Tα1 (BMJB024)

Use the same method as described in Example 1.1 to synthesize Ac-[$Cys^{24}$]Tα1, giving rise to crude peptide 162 mg. Purify it by RP-HPLC and analyze it by ESI-MS. $[M]^{3+}$ peak: 1029.0 (theoretical value: 3082).

Use the same method as described in Example 1.2 to synthesize Ac-[$Cys^{24}$(mPEG$_{5000}$-MAL)]Tα1. Purify the product by HPLC and lyophilize it, giving rise to 17.3 mg white solid with a yield of 37.4%.

Use MALDI-TOF-MS to analyze Ac-[$Cys^{24}$(mPEG$_{5000}$-MAL)]Tα1. There are several peaks around 8281, the difference of molecular weight between adjacent two peaks are about 44, which is the typical structural characteristic of polyethylene glycol.

Example 8

Interferon-γ Production of Spleen Cells Induced by Tα1, its Ac-[$Cys^x$]Tα1 Analogues and its PEG Modified Products Prepare spleen cell suspension in sterile condition. Adjust cell concentration to $5 \times 10^6$ cell/mL by adding RPMI-1640 culture with 20% bovine serum. Add 0.5 mL cell suspension, 0.25 mL Con A (final concentration is 0.5 μg/mL) and 0.25 mL samples with different concentrations in 24-well plate; and add RPMI-1640 culture in control wells. Incubate the plates in a 5% $CO_2$ chamber at 37° C. for 24 hours. Centrifuge and collect supernatant, test the content of IFN-γ in supernatant by double antibody sandwich ELISA. The protocol is according to the instruction on ELISA kit.

TABLE 1-1

Test results for IFN-γ production of spleen cell induced by Tα1 and analogues thereof stimulated by Con A stimulate (1)

| Group | Dose (μg/mL) | Concentration of IFN-γ (pg/mL) | Enhancement Percentage (%) |
|---|---|---|---|
| 1640 | — | 0 | |
| Con A | 0.5 | 751.7 ± 55.6 | 0 |
| Tα1 | 1 | 1449.3 ± 334.3* | +92.8 |
| | 10 | 1514.0 ± 102.1*** | +101.4 |
| | 100 | 1007.2 ± 31.3** | +34.0 |
| BMJBT009 | 1 | 1895.7 ± 49.8*** | +152.2 |
| | 10 | 1814.5 ± 105.5*** | +141.4 |
| | 100 | 672.1 ± 94.3 | −11.0 |
| BMJBT005 | 1 | 1822.2 ± 24.3*** | +142.4 |
| | 10 | 1706.5 ± 139.3*** | +127.0 |
| | 100 | 906.9 ± 10.7** | +20.6 |
| BMJB016 | 1 | 1426.8 ± 36.8*** | +89.8 |
| | 10 | 1295.7 ± 165.9** | +72.4 |
| | 100 | 455.5 ± 79.3**↓ | −39.4 |
| BMJB017 | 1 | 1048.9 ± 181.4* | +39.5 |
| | 10 | 856.4 ± 61.8 | +13.9 |
| | 100 | 474.7 ± 10.2**↓ | −36.9 |

Note:
Con A is added in every sample, n = 3,
*P < 0.05,
**P < 0.01,
***P < 0.001, analyzed by t test.

TABLE 1-2

Test results for IFN-γ production of spleen cell induced by Tα1 and modifications thereof stimulated by Con A (2)

| Group | Dose (μg/mL) | Concentration of IFN-γ (pg/mL) | Enhancement Percentage (%) |
|---|---|---|---|
| 1640 | — | 0 | |
| Con A | 0.5 | 3258.0 ± 44.7 | 0 |
| BMJBT001 | 1 | 3000.5 ± 56.1 | −7.9 |
| | 10 | 3584.2 ± 31.6*** | +10.0 |
| | 100 | 3618.5 ± 93.8** | +11.0 |
| BMJB012 | 1 | 4224.7 ± 183.1*** | +29.7 |
| | 10 | 3115.3 ± 377.1 | −4.4 |
| | 100 | 3277.7 ± 181.0 | +0.6 |
| BMJBT003 | 1 | 3428.6 ± 111.9 | +5.2 |
| | 10 | 3732.2 ± 30.2*** | +14.5 |
| | 100 | 3990.8 ± 250.0* | +22.5 |
| BMJB014 | 1 | 3616.4 ± 155.7* | +11.0 |
| | 10 | 3529.4 ± 216.0 | +8.3 |
| | 100 | 4211.8 ± 149.7*** | +29.3 |
| BMJBT004 | 1 | 3671.1 ± 86.0** | +12.7 |
| | 10 | 3216.1 ± 228.6 | −1.3 |
| | 100 | 3565.9 ± 77.8 | +0.5 |
| BMJB015 | 1 | 3908.2 ± 147.2** | +20.0 |
| | 10 | 3962.9 ± 137.6** | +21.6 |
| | 100 | 3526.2 ± 68.0 | +8.2 |

Note:
Con A is added in every sample, n = 3,
*P < 0.05,
**P < 0.01,
***P < 0.001, analyzed by t test.

TABLE 1-3

Test result for spleen cell products IFN-γ which induced by Tα1 and analogues thereof stimulated by Con A (3)

| Group | Dose (μg/mL) | Concentration of IFN-γ (pg/mL) | Enhancement percentage (%) |
|---|---|---|---|
| 1640 | — | 0 | |
| Con A | 0.5 | 3054.1 ± 308.4 | 0 |
| Tα1 | 1 | 3609.6 ± 167.8 | +18.2 |
| | 10 | 3891.5 ± 106.1* | +27.4 |
| | 100 | 4361.3 ± 87.8** | +42.8 |
| BMJBT008 | 1 | 4323.8 ± 187.0** | +41.6 |
| | 10 | 3115.0 ± 195.8 | +2.0 |
| | 100 | 2975.5 ± 182.6 | −2.6 |
| BMJB019 | 1 | 3392.9 ± 102.1 | +11.1 |
| | 10 | 3927.1 ± 230.9* | +28.6 |
| | 100 | 3910.3 ± 155.4* | +28.0 |
| BMJB020 | 1 | 3998.3 ± 157.7* | +30.9 |
| | 10 | 2654.0 ± 211.1 | −13.1 |
| | 100 | 3135.8 ± 195.4 | +2.7 |
| BMJB018 | 1 | 3730.3 ± 150.9* | +22.1 |
| | 10 | 3705.5 ± 121.2* | +21.3 |
| | 100 | 3880.6 ± 154.5* | +27.1 |

Note:
Con A is added in every sample, n = 3,
*P < 0.05,
**P < 0.01,
***P < 0.001, analyzed by t test.
Conclusion: After modified with PEG, Tα1 still has the activity to induce spleen cell to produce IFN-γ.

Example 9

Effect of T Lymphocyte Proliferation Stimulated by Tα1, Ac-[Cys$^x$]Tα1 Analogues and PEG Modifications Thereof Sacrifice mouse by draining artery blood, remove spleen in sterile condition, and make it to spleen cell suspension. After red blood cell lysis, wash for 3 times, and stain with Trypan Blue to count the living cells. The amount of living cells should be more than 95%. Dilute the cell concentration to $5×10^6$ cell/mL by adding RPMI-1640 culture with 10% bovine serum. Add spleen cell suspension to a sterilized 96-well plate for 100 μL per well. The total amount is 200 μL per well (including 50 μL Con A and 50 μL medicament). Each sample concentration is repeated fro 3-4 wells. Incubate the plate in a 5% $CO_2$ chamber for 72 hours, add 10 μci/mL $^3$H-TdR 20 μL per well 16 hours before termination of the incubation, giving rise to a final concentration of 1.0 μci (37.0 KBq)/mL. Collect cells on filter membrane by using Herveste 96 cell harvester, dried in 80° C. oven for 20 minutes or dried in air. Put the dried filter membrane into 1450-423 microBeta sample bag, add scintillation liquid, and measure radioactivity (cpm) in Perkin Elmer MicroBeta Trilux 1450 Scintillation Counter.

TABLE 2-1

Test results for proliferation of T lymphocyte induced by Tα1 and PEG modifications thereof stimulated by Con A (1)

| Group | Concentration (μg/mL) | $^3$H-TdR incorporation (cpm, x ± SD) | Enhancement percentage (%) |
|---|---|---|---|
| 1640 (−) | 0 | 278 ± 53 | |
| Con A (+) | 0.5 | 13487 ± 3544 | 0 |
| Tα1 | 10 | 17871 ± 4635 | +32.5 |
| | 50 | 17007 ± 1526 | +26.1 |
| | 100 | 14624 ± 3253 | +6.6 |

TABLE 2-1-continued

Test results for proliferation of T lymphocyte induced by Tα1
and PEG modifications thereof stimulated by Con A (1)

| Group | Concentration (μg/mL) | $^3$H-TdR incorporation (cpm, x ± SD) | Enhancement percentage (%) |
|---|---|---|---|
| BMJBT009 | 10 | 24888 ± 2473** | +84.5 |
|  | 50 | 24164 ± 2683** | +46.6 |
|  | 100 | 20574 ± 2746* | +56.6 |
| BMJBT005 | 10 | 22237 ± 5551* | +64.9 |
|  | 50 | 22413 ± 1436** | +66.2 |
|  | 100 | 17551 ± 2491 | +30.1 |
| BMJB016 | 10 | 21697 ± 3489* | +60.9 |
|  | 50 | 22584 ± 1463** | +67.4 |
|  | 100 | 20708 ± 1211** | +53.5 |
| BMJBT006 | 10 | 21152 ± 2936* | +56.8 |
|  | 50 | 19880 ± 1777* | +47.4 |
|  | 100 | 14319 ± 2333 | +6.2 |
| BMJB017 | 10 | 18919 ± 3507 | +40.3 |
|  | 50 | 21091 ± 3916* | +56.4 |
|  | 100 | 16778 ± 2483 | +24.4 |

Note:
Con A is added in every sample, n = 4,
*P < 0.05,
**P < 0.01,
***P < 0.001, analyzed by t test.

TABLE 2-2

Test results for proliferation of T lymphocyte induced by Tα1
and PEG modifications thereof stimulated by Con A (2)

| Group | Concentration (μg/mL) | $^3$H-TdR incorporation (cpm, x ± SD) | Enhancement percentage (%) |
|---|---|---|---|
| 1640 (−) | 0 | 184 ± 5 |  |
| Con A (+) | 0.5 | 11642 ± 2067 | 0 |
| Tα1 | 10 | 18315 ± 2194** | +57.3 |
|  | 50 | 17007 ± 1526** | +46.1 |
|  | 100 | 14383 ± 3225 | +23.5 |
| BMJBT001 | 10 | 19289 ± 4456* | +65.7 |
|  | 50 | 19972 ± 3287** | +71.6 |
|  | 100 | 21119 ± 5339* | +81.4 |
| BMJB012 | 10 | 22772 ± 3222** | +95.6 |
|  | 50 | 24066 ± 4004** | +106.7 |
|  | 100 | 25176 ± 3656*** | +116.3 |
| BMJBT002 | 10 | 23881 ± 2809*** | +105.1 |
|  | 50 | 19611 ± 2612** | +68.5 |
|  | 100 | 11956 ± 1555 | +2.6 |
| BMJB013 | 10 | 25396 ± 1081*** | +118.1 |
|  | 50 | 20568 ± 2179** | +76.7 |
|  | 100 | 20091 ± 1640*** | +72.6 |
| BMJBT003 | 10 | 21825 ± 2216*** | +87.5 |
|  | 50 | 20465 ± 2432** | +77.3 |
|  | 100 | 15240 ± 2369 | +30.9 |
| BMB014 | 10 | 22381 ± 3227** | +92.2 |
|  | 50 | 21289 ± 3023** | +82.9 |
|  | 100 | 14773 ± 2872 | +26.9 |

Note:
Con A is added in every sample, n = 4,
*P < 0.05,
**P < 0.01,
***P < 0.001, analyzed by t test
Conclusion: After modified with PEG, Tα1 still shows potent proliferative effect to spleen cell.

Example 10

The Dynamic Process of Plasma Concentration of Tα1, Analogues of Ac-[Cys$^x$]Tα1 and PEG Modifications Thereof in Mouse Coating antigen: Dilute Tα1 detection antigen stock solution to a final concentration of 2 μg/mL with coating solution, and add it into the wells of ELISA plate for 0.1 mL per well, and incubate at 4° C. for 5 days. Then wash the ELISA plate 3 times with washing buffer, each 0.2 mL/well and 3 min/time. Add 0.2 mL blocking buffer to each well, incubate for 1.5 hours at 37° C., wash plate 2 times by washing buffer, and spin dried.

Sample preparation: Weight sample accurately, dissolve it in saline to a concentration of 1.5 mg/mL. Administrate 0.2 Ml by injection to each mouse peritoneally. Collect blood sample in 3 min, 20 min, 40 min, 1 h, 2 h, 3 h, 6 h, 8 h, 12 h, and 24 h. Collect serum by centrifuge the blood samples for 5 minutes at 10000 rpm, stored at −20° C. in a freezer. o prepare test sample, 0.2 mL sample was added by 0.1 mL 1:1500 rabbit anti-Tα1 serum (final concentration is 1:6000), and 0.2 mL CD-1® mouse serum, and 0.1 mL PBS with 1% skimmed milk. Prepare blank control at the same time. Total volume is 0.4 mL. Incubate for 2 hours at 37° C. To prepare standard sample, Tα1 0.1 mL with different concentrations from 0.0004 to 400 μg/mL was added by 0.1 mL 1:1500 rabbit anti-Tα1 serum (final concentration is 1:6000), and 0.2 mL CD-1® mouse serum. Prepare blank control at the same time. Total volume is 0.4 mL. Incubate for 2 hours at 37° C.

Sample Testing Add the prepared test sample and standard sample to ELISA plate, 0.1 mL/well, reacting for 1 hour in 37° C. chamber. Wash the plates 3 times, spin dryed. Add substrate 0.1 mL/well for 10 minutes. Add 2 mol/L $H_2SO_4$ 0.05 mL to each well to terminate the reaction. Measure the OD value at 450 nm. Plot the standard curve with the concentration of Tα1 standard sample as abscissa and OD value as vertical coordinate. Calculate the content of test sample according to this standard curve.

Figure 2:
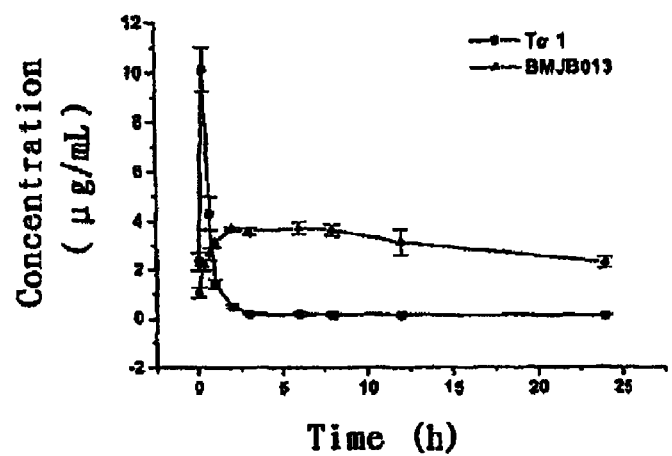
FIG. 2 Plasma concentration—time curve of Tα1 and its PEG modification BMJB013 in mouse.
Figure 3:
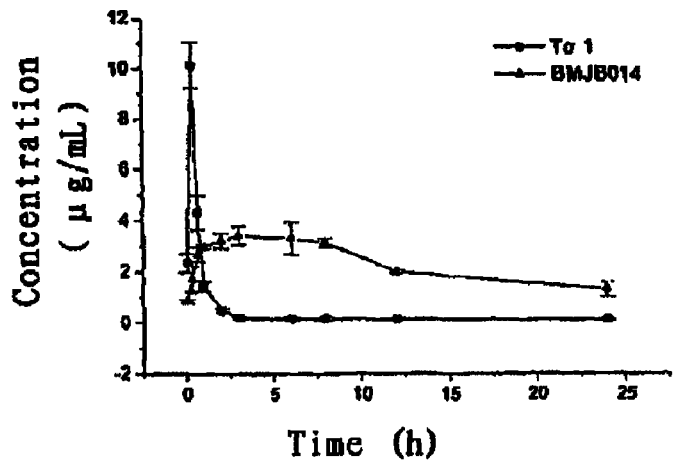
FIG. 3 Plasma concentration—time curve of Tα1 and its PEG modification BMJB014 in mouse.
Figure 4:
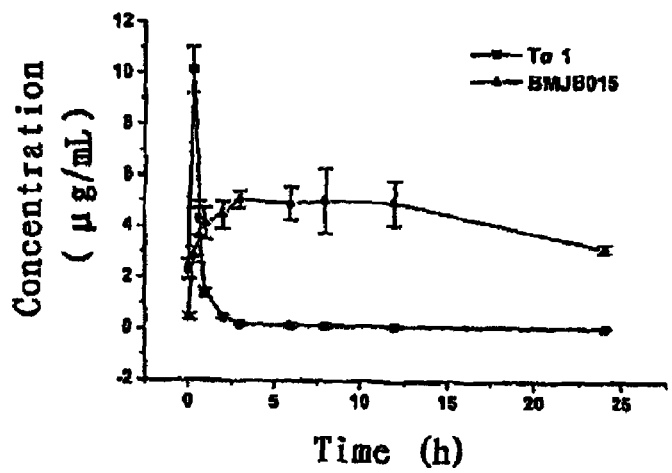
FIG. 4 Plasma concentration—time curve of Tα1 and its PEG modification BMJB015 in mouse.
Figure 5:
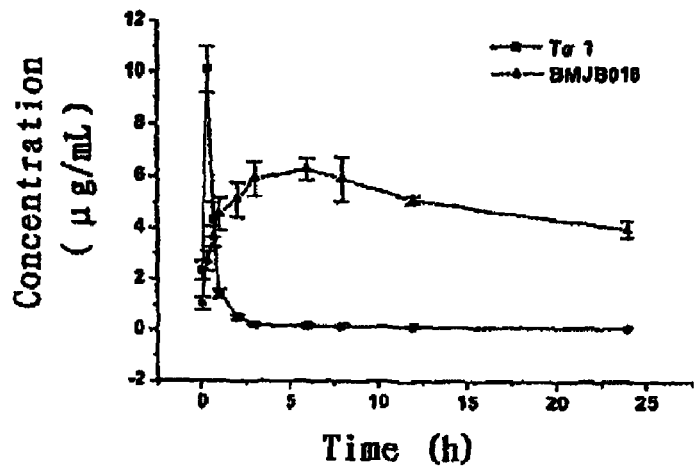
FIG. 5 Plasma concentration—time curve of Tα1 and its PEG modification BMJB016 in mouse.
Figure 6:
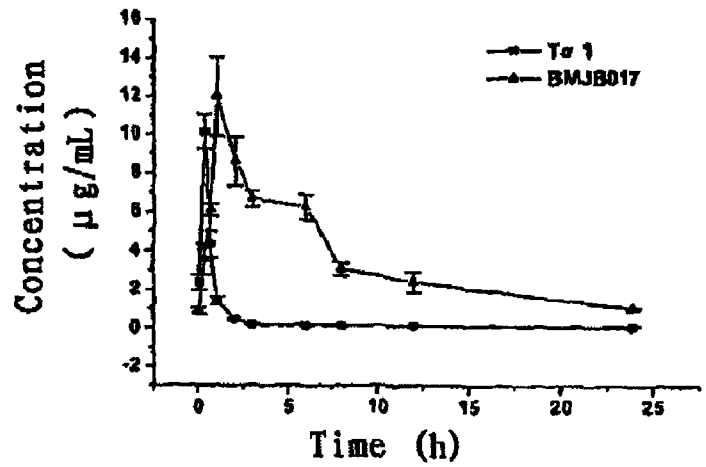
FIG. 6 Plasma concentration—time curve of Tα1 and its PEG modification BMJB017 in mouse.
Figure 7:
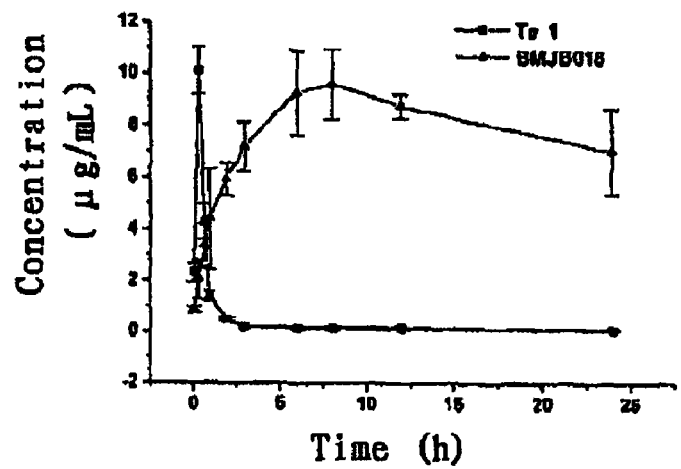
FIG. 7 Plasma concentration—time curve of Tα1 and its PEG modification BMJB018 in mouse.
Figure 8:
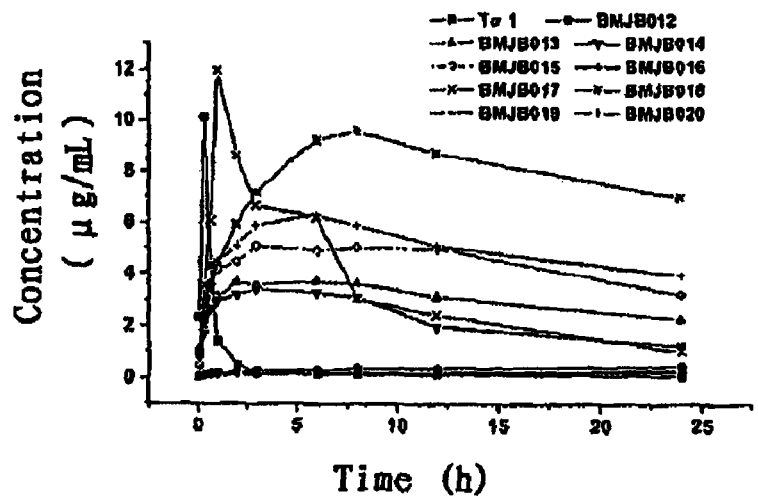
FIG. 8 Plasma concentration—time curve of Tα1 and its PEG modifications in mouse.
Figure 9:
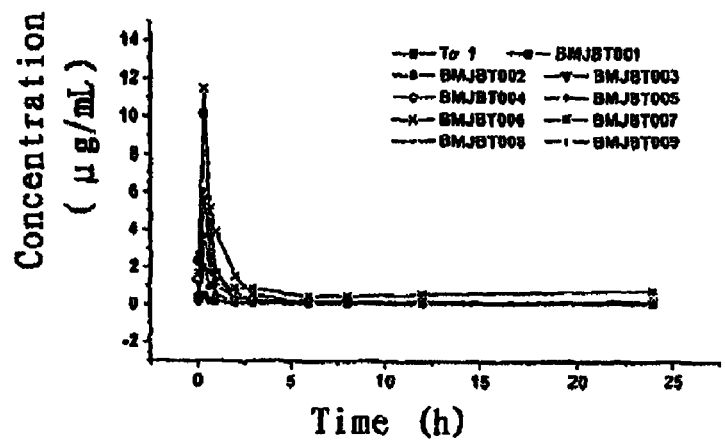
FIG. 9 Plasma concentration—time curve of Tα1 and its analogues in mouse.

Table 5 lists the pharmacokinetic parameters. FIG. 1 to FIG. 12 are concentration—time curves for Tα1 and its PEG modifications. Comparing with Tα1, it is concluded that Tα1-PEGs has better bioavailability and longer duration in vivo.

TABLE 5

Pharmacokinetics* of Tα1 and modifications thereof in mouse

| Compounds | Pharmacokinetic parameters | | |
|---|---|---|---|
|  | AUC (g · h/L) | $C_{max}$ (μg/mL) | $T_{max}$ (h) |
| Tα1 | 9.219 | 10.120 | 0.333 |
| BMJBT001 | 3.090 | 0.448 | 0.333 |
| BMJBT002 | 2.437 | 1.864 | 0.333 |
| BMJBT003 | 8.711 | 5.649 | 0.333 |
| BMJBT004 | 8.762 | 4.943 | 0.333 |
| BMJBT005 | 6.113 | 3.650 | 0.333 |
| BMJBT006 | 12.760 | 11.480 | 0.333 |
| BMJBT007 | 17.860 | 5.992 | 0.333 |
| BMJBT008 | 1.210 | 0.430 | 0.333 |
| BMJBT009 | 2.117 | 0.443 | 1.000 |
| BMJB012 | 8.146 | 0.348 | 12.000 |
| BMJB013 | 73.460 | 3.713 | 6.000 |
| BMJB014 | 54.410 | 3.396 | 3.000 |
| BMJB015 | 106.400 | 5.082 | 3.000 |
| BMJB016 | 120.300 | 6.289 | 6.000 |
| BMJB017 | 83.480 | 11.980 | 1.000 |
| BMJB018 | 189.400 | 9.612 | 8.000 |
| BMJB019 | 5.269 | 0.211 | 12.000 |
| BMJB020 | 4.076 | 0.172 | 12.000 |

*Pharmacokinetic parameters in 24 h, n = 3, each mouse was administrated for the sample 300 μg.

Example 6

Half-Life of Tα1 and its PEG Modified Products of the Invention in Liver Homogenate Experimental method: Prepare 0.4 mg/mL or 0.8 mg/mL sample aqueous solution in centrifuge tube, adding 50 μL liver homogenate. Then incubate for different time in 37° C. water bath. Terminate the reaction and precipitate liver homogenate protein by heating the mixture in boiling water for 5 minutes. Centrifuge it (10000 rpm) for 10 minutes. Analyze the supernatant by HPLC. The data was statistically analyzed by Origin Prof. 5.0.

HPLC: Column temperature: 25° C.; Flow rate 1.0 mL/min; Detection wavelength: 200 nm; Mobile phase A: 0.1% TFA/$H_2O$; Mobile phase B: 0.1% TFA/70% $CH_3CN$.

Results were listed in Table 6.

TABLE 6

Half-life of Tα1 and its PEG modified products in liver homogenate

| Sample | $t_{1/2}$ (h) | Sample | $t_{1/2}$ (h) |
|---|---|---|---|
| Tα1 | 4.2 | | |
| BMJBT001 | 3.8 | BMJB001 | 142.9 |
| BMJBT002 | 2.1 | BMJB002 | 125.0 |
| BMJBT003 | 2.8 | BMJB003 | 136.4 |
| BMJBT004 | 0.8 | BMJB004 | 130.0 |
| BMJBT005 | 2.8 | BMJB005 | 250.0 |
| BMJBT006 | 2.6 | BMJB006 | 136.4 |
| BMJBT007 | 0.5 | BMJB007 | 176.5 |
| BMJBT008 | <1.0 | BMJB008 | 65.2 |
| BMJBT009 | 0.4 | BMJB009 | 88.2 |

Comparing to the half-life of Tα1, the half-life of Tα1-PEGs are significantly prolonged. The half-lifes of Tα1-PEGs are 15.5-59.5 folds of that of Tα1. This shows that Tα1-PEGs has better enzyme stability than Tα1.

The invention claimed is:

1. A compound of formula (I):

wherein:

Z is H, methyl, ethyl, propyl, isopropyl, butyl, pentyl, isopentyl, formyl, acetyl, propionyl, carbamoyl, benzyloxycarbonyl, or fluorenylformyl;

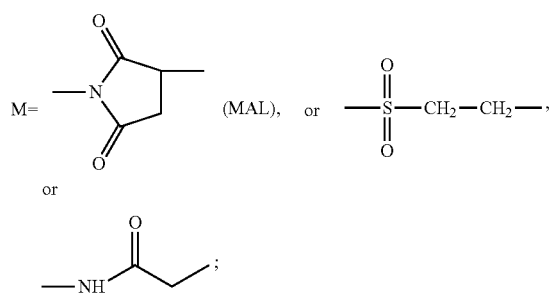

PEG is $RO(CH_2CH_2O)_m$—$CH_2CH_2$—, R═H or $CH_3$, m=5-2000;

Cys is cysteine and covalently linked with M group via side chain sulfide atom;

T represents a natural Tα1 complete sequence or an analogue thereof in which any site is substituted by at least one Cys, and the N-terminal of T or analogue thereof is acetylated;

x represents the site of Cys in T, and x=5-24;

Aa represents any one of 20 natural amino acids or the combination thereof, n=0-10.

2. A compound according to claim 1, wherein the sequence comprising Tα1 and Cys derivatives thereof is represented by the following formulas:

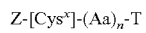

when n=0, Cys can be at any sites where x=5-24;

when n=1-10, Aa is one of 20 natural amino acids or a combination thereof;

wherein said natural amino acids include Ala, Arg, Asn, Asp, Cys, Gln, Glu, Gly, His, Ile, Leu, Lys, Met, Phe, Pro, Ser, Thr, Trp, Tyr, or Val.

3. A compound according to claim 1, wherein the compounds are:

Ac-[$Cys^5$(m$PEG_{5000}$-MAL)]Tα1,
Ac-[$Cys^8$(m$PEG_{5000}$-MAL)]Tα1,
Ac-[$Cys^{11}$(m$PEG_{5000}$-MAL)]Tα1,
Ac-[$Cys^{16}$(m$PEG_{5000}$-MAL)]Tα1,
Ac-[$Cys^{17}$(m$PEG_{5000}$-MAL)]Tα1,
Ac-[$Cys^{21}$(m$PEG_{5000}$-MAL)]Tα1,
Ac-[$Cys^{24}$(m$PEG_{5000}$-MAL)]Tα1.

4. A pharmaceutical composition comprising at least one compound of formula (I) according to claim 1 and pharmaceutically acceptable carriers or excipients.

5. A method for the treatment of hepatitis B or hepatitis C said method comprises administrating alone or in combination with other medicaments to a patient a compound of formula (I) according to any one of claims 1 to 3.

6. A compound of formula (I):

wherein:

Z is H, methyl, ethyl, propyl, isopropyl, butyl, pentyl, isopentyl, formyl, acetyl, propionyl, carbamoyl, benzyloxycarbonyl, or fluorenylformyl;

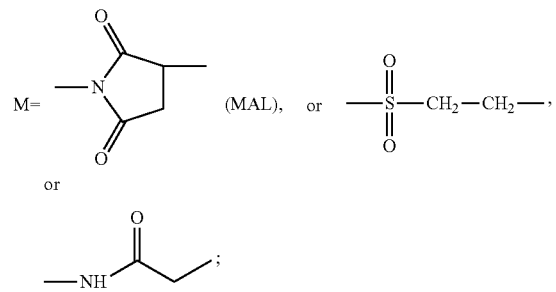

PEG is $RO(CH_2CH_2O)_m$—$CH_2CH_2$—, R═H or $CH_3$, m=5-2000;

Cys is cysteine and covalently linked with M group via side chain sulfide atom;

T represents a natural Tα1 complete sequence or an analogue thereof in which any site is substituted by at least one Cys, and the N-terminal of T or analogue thereof is acetylated;

x represents the site of Cys in T, and x=2-28;

Aa represents any one of 20 natural amino acids or the combination thereof, n=0-10.

7. A compound according to claim 6, wherein the sequence comprising Tα1 and Cys derivatives thereof is represented by the following formulas:

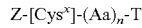

when n=0, Cys can be at any sites where x=5-24;

when n=1-10, Aa is one of 20 natural amino acids or a combination thereof;

wherein said natural amino acids include Ala, Arg, Asn, Asp, Cys, Gln, Glu, Gly, His, Ile, Leu, Lys, Met, Phe, Pro, Ser, Thr, Trp, Tyr, or Val.

8. A compound according to claim 6, wherein the compounds are:

Ac-[Cys$^5$(mPEG$_{5000}$-MAL)]Tα1,
Ac-[Cys$^8$(mPEG$_{5000}$-MAL)]Tα1,
Ac-[Cys$^{11}$(mPEG$_{5000}$-MAL)]Tα1,
Ac-[Cys$^{16}$(mPEG$_{5000}$-MAL)]Tα1,
Ac-[Cys$^{17}$(mPEG$_{5000}$-MAL)]Tα1,
Ac-[Cys$^{21}$(mPEG$_{5000}$-MAL)]Tα1,
Ac-[Cys$^{24}$(mPEG$_{5000}$-MAL)]Tα1.

9. A pharmaceutical composition comprising at least one compound of formula (I) according to claim 6 and pharmaceutically acceptable carriers or excipients.

10. A method for the treatment of hepatitis B or hepatitis C said method comprises administrating alone or in combination with other medicaments to a patient a compound of formula (I) according to any one of claims 6 to 8.

11. A compound according to claim 1, wherein Z is acetyl or carbamoyl.

12. A compound according to claim 1, wherein Aa is Gly, Ala, Val, Leu, or any combination thereof.

13. A compound according to claim 6, wherein Z is acetyl or carbamoyl.

14. A compound according to claim 6, wherein Aa is Gly, Ala, Val, Leu, or any combination thereof.

\* \* \* \* \*

UNITED STATES PATENT AND TRADEMARK OFFICE
CERTIFICATE OF CORRECTION

PATENT NO. : 8,080,522 B2  
APPLICATION NO. : 12/093240  
DATED : December 20, 2011  
INVENTOR(S) : Liu et al.

Page 1 of 1

It is certified that error appears in the above-identified patent and that said Letters Patent is hereby corrected as shown below:

Title Page,

Item (22) PCT Filed: "Nov. 11, 2006" should read --Nov. 10, 2006--.

Signed and Sealed this
Sixteenth Day of April, 2013

Teresa Stanek Rea
*Acting Director of the United States Patent and Trademark Office*